(12) United States Patent
Trautman

(10) Patent No.: US 7,407,499 B2
(45) Date of Patent: Aug. 5, 2008

(54) OSMOTIC PUMP WITH SELF-RETAINING, FAST-START MEMBRANE PLUG

(75) Inventor: Joseph C. Trautman, Sunnyvale, CA (US)

(73) Assignee: Intarcia Therapeutics, Inc., Hayward, CA (US)

(*) Notice: Subject to any disclaimer, the term of this patent is extended or adjusted under 35 U.S.C. 154(b) by 200 days.

(21) Appl. No.: 10/969,753

(22) Filed: Oct. 20, 2004

(65) Prior Publication Data
US 2005/0095284 A1 May 5, 2005

Related U.S. Application Data

(60) Provisional application No. 60/517,220, filed on Oct. 31, 2003.

(51) Int. Cl.
*A61K 9/22* (2006.01)
(52) U.S. Cl. .................. 604/892.1; 604/890.1; 424/422
(58) Field of Classification Search ............. 604/892.1, 604/890.1, 891.1; 424/472, 422
See application file for complete search history.

(56) References Cited

U.S. PATENT DOCUMENTS

| | | | | |
|---|---|---|---|---|
| 3,025,991 A | * | 3/1962 | Gillon | 215/311 |
| 4,969,884 A | * | 11/1990 | Yum | 604/892.1 |
| 5,985,305 A | * | 11/1999 | Peery et al. | 424/422 |
| 6,113,938 A | | 9/2000 | Chen | |
| 6,270,787 B1 | | 8/2001 | Ayer | |
| 6,287,295 B1 | * | 9/2001 | Chen et al. | 604/892.1 |
| 6,524,305 B1 | | 2/2003 | Peterson et al. | |

FOREIGN PATENT DOCUMENTS

| | | |
|---|---|---|
| WO | WO 99/04767 | 2/1999 |
| WO | WO 99/33449 | 7/1999 |

* cited by examiner

*Primary Examiner*—Kevin C. Sirmons
*Assistant Examiner*—Phillip Gray
(74) *Attorney, Agent, or Firm*—Barbara G. McClung; Gary R. Fabian

(57) ABSTRACT

An osmotic pump includes a capsule having at least one delivery port formed at a first end and a membrane plug retained in a second end of the capsule remote from the delivery port to provide a fluid-permeable barrier between an interior and an exterior of the capsule. The membrane plug has a columnar body and at least one slot formed in the columnar body to vent pressure from the interior to the exterior of the capsule when the columnar body extends a predetermined distance relative to the second end of the capsule, thereby preventing expulsion of the membrane plug from the second end.

19 Claims, 3 Drawing Sheets

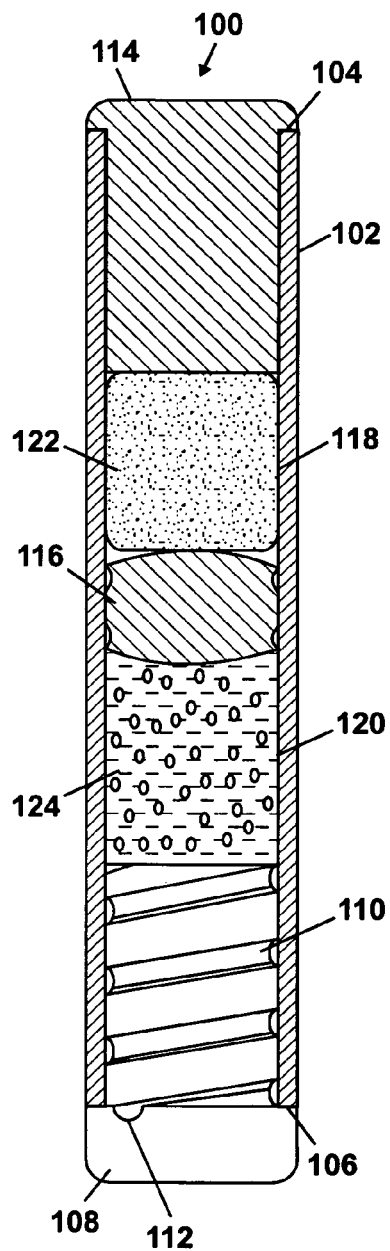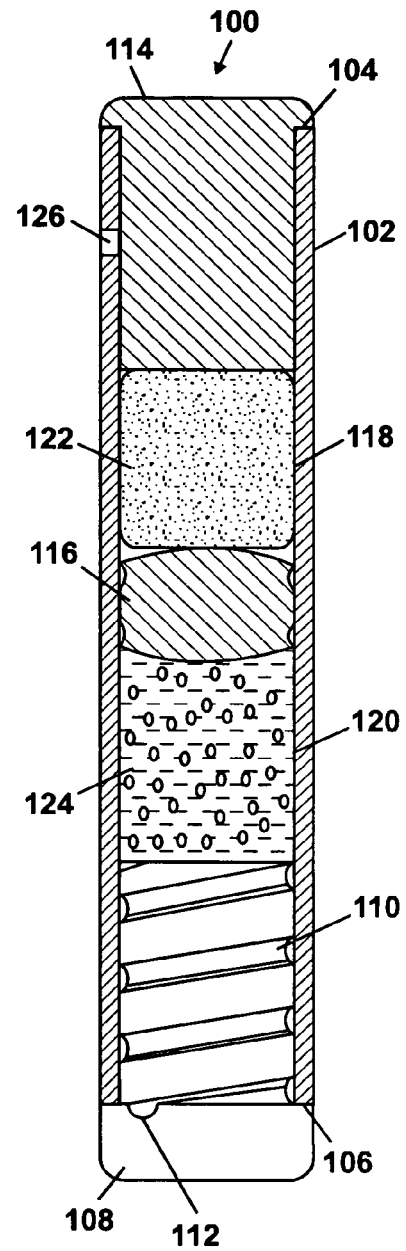
(PRIOR ART)
FIG. 1A
(PRIOR ART)
FIG. 1B

OSMOTIC PUMP WITH SELF-RETAINING, FAST-START MEMBRANE PLUG

CROSS-REFERENCE TO RELATED APPLICATIONS

This application claims the benefit of U.S. Provisional Application No. 60/517,220, filed Oct. 31, 2003.

BACKGROUND OF THE INVENTION

The invention relates generally to osmotic pumps for delivering beneficial agents. More specifically, the invention relates to an osmotic pump having a membrane plug for controlling the delivery rate of a beneficial agent.

Osmotic pumps for delivering beneficial agents within the body of a patient are known in the art. For illustration purposes, FIG. 1A shows a cross-section of a prior-art osmotic pump 100 having an implantable capsule 102 with open ends 104, 106. A diffusion moderator (also called flow modulator) 108 is disposed in the open end 106 of the capsule 102. The diffusion moderator 108 has a delivery path 110 that terminates at a delivery port 112 and allows fluid from the interior of the capsule 102 to be transported to the exterior of the capsule 102. A membrane plug 114 is inserted in the open end 104 of the capsule 102. The membrane plug 114 is made of a semipermeable material and forms a fluid-permeable barrier between the exterior and the interior of the capsule 102. A piston 116 is disposed in the capsule 102. The piston 116 defines two chambers 118, 120 within the capsule 102. The chamber 118 contains an osmotic agent 122, and the chamber 120 contains a beneficial agent 124.

When the osmotic pump 100 is implanted in a patient, fluid from the body of the patient enters the chamber 118 through the membrane plug 114, permeates the osmotic agent 122, and causes the osmotic agent 122 to swell. The swollen osmotic agent 122 pushes the piston 116 in a direction away from the membrane plug 114, reducing the volume of the chamber 120 and forcing an amount of the beneficial agent 124 out of the capsule 102 through the diffusion moderator 108 into the body of the patient. The rate at which the osmotic pump 100 delivers the beneficial agent 124 to the body depends on the rate at which fluid permeates the membrane plug 114.

Typically, the membrane plug 114 is made of a hydratable compound that must hydrate in order for the osmotic agent 122 to begin absorbing moisture. The time to hydrate the membrane plug 114 and the osmotic agent 122 delays the start of ejection of the beneficial agent 124 from the chamber 120. During this startup phase, body fluid, usually water, can back-diffuse into the delivery port 112 of the diffusion moderator 108 and degrade the beneficial agent 124 or the vehicle carrying the beneficial agent 124. Some vehicles when they combine with water can plug the delivery path 110.

If the delivery path 110 or port 112 becomes plugged, for example, due to a lengthy startup, or if the piston 116 becomes stuck inside the capsule 102, there will be pressure buildup in the chamber 118, which may be sufficient to expel the membrane plug 114 from the capsule 102.

Various methods have been proposed for avoiding expulsion of the membrane plug 114 from the capsule 102. One method involves securing the membrane plug 114 to the capsule 102 using an adhesive. This method requires an additional operation to apply the adhesive to the membrane plug 114 and/or the capsule 102, and the adhesive may affect the permeability of the membrane plug 114. Another method for avoiding expulsion of the membrane plug 114 is to drill a hole in the end portion of the capsule 102 containing the membrane plug 114. FIG. 1B shows a hole 126 drilled in the capsule 102. As shown in FIG. 1B, the hole 126 is initially covered by the membrane plug 114, but as the membrane plug 114 is forced out of the capsule 102 due to pressure buildup in the chamber 118, the hole 126 will eventually become exposed, allowing pressure to be vented from the chamber 118 to the exterior of the capsule 102. In this manner, the membrane plug 114 is prevented from becoming separated from the capsule 102. This method requires an additional operation in the fabrication of the capsule 102 and increases the overall cost of the osmotic pump.

BRIEF SUMMARY OF THE INVENTION

In one aspect, the invention relates to an osmotic pump which comprises a capsule having at least one delivery port formed at a first end and a membrane plug retained in a second end of the capsule remote from the delivery port to provide a fluid-permeable barrier between an interior and an exterior of the capsule. The membrane plug has a columnar body and at least one slot formed in the columnar body to vent pressure from the interior to the exterior of the capsule when the columnar body extends a predetermined distance relative to the second end of the capsule, thereby preventing expulsion of the membrane plug from the second end.

In another aspect, the invention relates to a membrane plug for use with an osmotic pump having a delivery capsule. The membrane plug comprises a columnar body made of a semipermeable material and having an outer surface for engagement with an inner surface of the capsule. The columnar body is provided with at least one slot, which extends from a base of the columnar body to a non-basal point on the outer surface of the columnar body so that pressure can be selectively vented from an interior to an exterior of the capsule.

In yet another aspect, the invention relates to a membrane plug for use with an osmotic pump having a delivery capsule which comprises a columnar body made of a semipermeable material. The columnar body has an outer surface for engagement with an inner surface of the capsule and is provided with an orifice that allows fluid flow into the capsule until the orifice becomes occluded due to swelling of the semipermeable material.

Other features and advantages of the invention will be apparent from the following description and the appended claims.

BRIEF DESCRIPTION OF THE DRAWINGS

FIGS. 1A and 1B are cross-sections of prior-art osmotic pumps.

DETAILED DESCRIPTION OF THE INVENTION

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

Figure 2A:
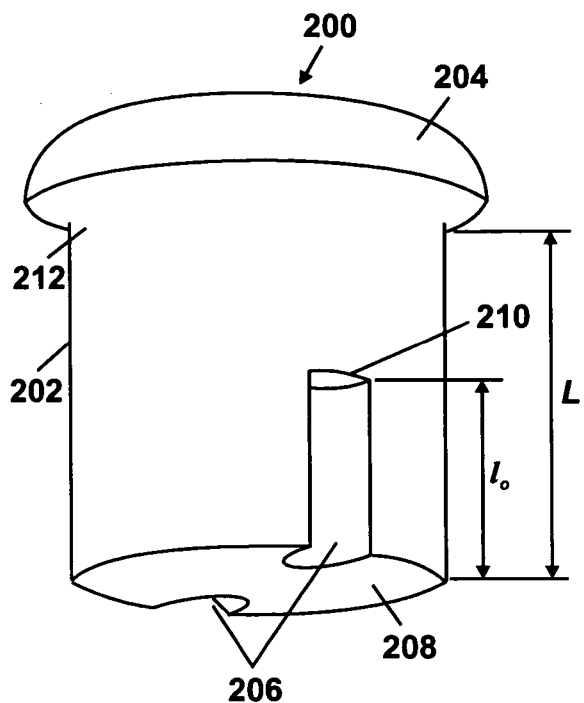
FIG. 2A is an enlarged view of a membrane plug according to an embodiment of the invention.

FIG. 2A shows a membrane plug 200 according to an embodiment of the invention. The membrane plug 200 can be inserted into an open end of an osmotic pump capsule (not shown) to control the rate at which fluid enters the capsule. The membrane plug 200 has a columnar body 202. The outer diameter of the columnar body 202 is selected such that the columnar body 202 can fit into the capsule. In one embodiment, the columnar body 202 terminates in an enlarged end cap 204. When the membrane plug 200 is inserted in the capsule, the end cap 204 acts as a stop member engaging an end of the capsule and achieving a repeatable position of the membrane plug 200 inside the capsule. In an alternative embodiment, the end cap 204 may be omitted, allowing the membrane plug 200 to be fully inserted into the capsule.

One or more slots 206 are formed in the columnar body 202. In one embodiment, the slots 206 are longitudinal, extending from the base 208 of the columnar body 202 to a point 210 below the end cap 204. In alternative embodiments, the slot(s) formed in the columnar body 202 may have other shapes. For example, a helical slot extending from the base 208 of the columnar body 202 to a point below the end cap 204 could be formed. Measured from the base 208 of the columnar body 202, the extent or height ($l_o$) of the slot(s) 206 may be in a range from about 10 to 90% of the length (L) of the columnar body 202, preferably in a range from about 20 to 80% of the length of the columnar body 202, more preferably in a range from about 30 to 60% of the length of the columnar body 202. In general, the extent or height ($l_o$) of the slot(s) 206 should be selected such that there is adequate (uninterrupted) sealing surface at the top portion 212 of the columnar body 202. The depth and width of the slot(s) 206 can be variable. In general, the depth and width should be selected such that the structural integrity of the membrane plug 200 is not compromised in use. The depth and width of the slot(s) 206 should be sufficiently large to be reproducibly formed in the columnar body 202 and to prevent occlusion of the slot due to swelling of the membrane material when hydrated. The depth of the slot(s) 206 can be in a range from approximately 1 to 99% of the diameter of the columnar body 202, preferably in a range from approximately 10 to 90% of the diameter of the columnar body 202. The width of the slot(s) 206 can be in a range from approximately 1 to 99% of the diameter of the columnar body 202, preferably in a range from approximately 10 to 90% of the diameter of the columnar body 202.

Figure 2B:
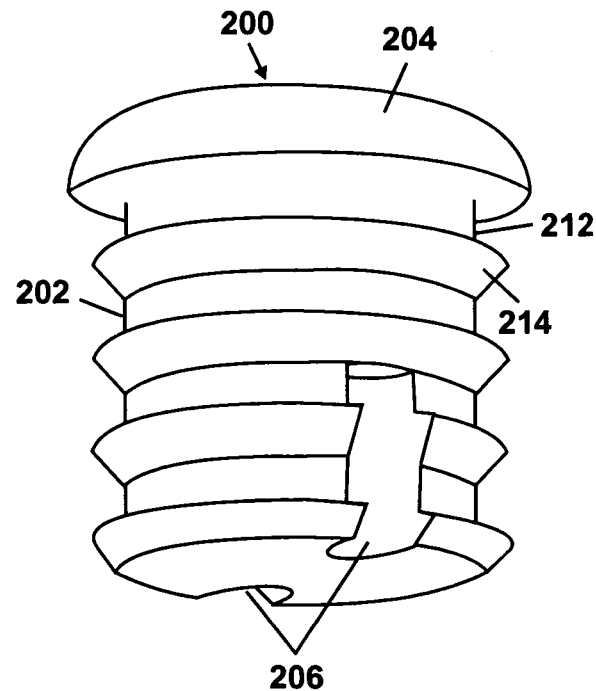
FIG. 2B is an enlarged view of a membrane plug according to another embodiment of the invention.

Protrusions, such as ribs, ridges, threads, or the like, may be formed on the columnar body 202 to enhance sealing between the columnar body 202 and the osmotic pump capsule (not shown), as taught by Chen et al. in U.S. Pat. No. 6,113,938. FIG. 2B shows circumferential ribs 214 formed on the columnar body 202 with the slots 206 cutting through the ribs 214. Preferably, the length of the slot(s) 206 is such that there are continuous ribs 214 in the top portion 212 of the columnar body 202 to ensure proper sealing between the top portion 212 and the inner surface of the osmotic pump capsule.

The membrane plug 200 is made of a semipermeable material that allows fluid, usually water, to pass into the interior of an osmotic pump capsule while preventing compositions within the capsule from passing out of the capsule. Semipermeable materials suitable for use in the invention are well known in the art. Semipermeable materials for the membrane plug 200 are those that can conform to the shape of the capsule upon wetting and that can adhere to the inner surface of the capsule. Typically, these materials are polymeric materials, which can be selected based on the pumping rates and system configuration requirements, and include, but are not limited to, plasticized cellulosic materials, enhanced PMMAs such as hydroxyethylmethacrylate (HEMA), and elastomeric materials such as polyurethanes and polyamides, polyether-polyamind copolymers, thermoplastic copolyesters, and the like.

Figure 3:
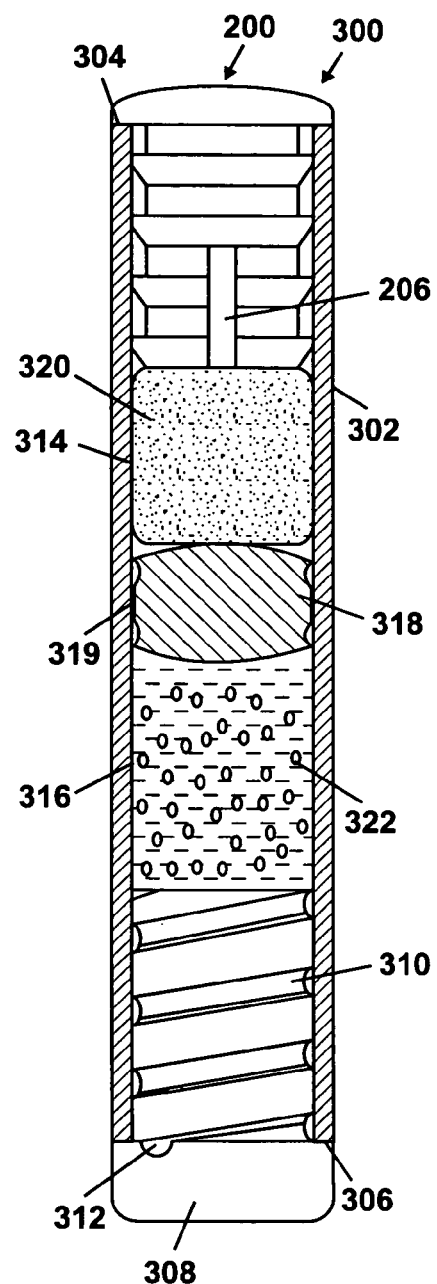
FIG. 3 shows an osmotic pump incorporating an embodiment of the membrane plug of the present invention.

FIG. 3 shows the membrane plug 200 used in an osmotic pump 300. It should be noted that the internal structure of the osmotic pump 300 is presented for illustration purposes only and is not to be construed as limiting the present invention. The present invention is generally applicable to all osmotic pumps having any number of shapes, and to all such pumps administered in implantable osmotic delivery techniques.

The osmotic pump 300 includes an elongated cylindrical capsule 302, which may be sized such that it can be implanted within a body. The capsule 302 has open ends 304, 306. The membrane plug 200 is inserted in the open end 304, and a diffusion moderator (or flow modulator) 308 is inserted in the open end 306. The diffusion moderator 308 includes a delivery path 310 which terminates in a delivery port 312. Although not shown, the diffusion moderator 308 may also include a vent hole and optionally a fill hole, as taught by Peterson et al. in U.S. Pat. No. 6,524,305. In an alternative embodiment, the diffusion moderator 308 could be omitted, and the open end 306 could be replaced with a closed end having a delivery port. The diffusion moderator 308 (or delivery port) allows fluid from within the capsule 302 to be delivered to the exterior of the capsule 302, while the membrane plug 200 allows fluid from the exterior of the capsule 302 to enter the interior of the capsule 302.

Two chambers 314, 316 are defined inside the capsule 302. The chambers 314, 316 are separated by a piston 318, which is configured to fit within the capsule 302 in a sealing manner and to move longitudinally within the capsule 302. The piston 318 may be made of an impermeable resilient material. As an example, the piston 318 may include annular ring shape protrusion(s) 319 that form a seal with the inner surface of the capsule 302. An osmotic agent 320 is disposed in the chamber 314 adjacent the membrane plug 200, and a beneficial agent 322 to be delivered to a body is disposed in the chamber 316 adjacent the diffusion moderator 308. The piston 318 isolates the beneficial agent 322 from the environmental liquids that are permitted to enter the capsule 302 through the membrane plug 200 such that in use, at steady-state flow, the beneficial agent 322 is expelled through the delivery port 312 at a rate corresponding to the rate at which liquid from the environment of use flows into the osmotic agent 320 through the membrane plug 200.

In operation, fluid enters the chamber 314 through the membrane plug 200 and permeates the osmotic agent 320. The wetted osmotic agent 320 swells and pushes the piston 318 in a direction away from the membrane plug 200, reducing the volume of the chamber 316 and forcing an amount of the beneficial agent 322 out through the diffusion moderator 308. If the diffusion moderator 308 becomes plugged or the piston 318 becomes stuck, pressure will build up in the chamber 314. This pressure buildup will force the membrane plug 200 in a direction away from the piston 318. The membrane plug 200 will slide out of the capsule 302 until the slot(s) 206 are exposed. As soon as the slots 206 are exposed, pressure from the chamber 314 will escape to the exterior of the capsule 302, thereby preventing further movement of the membrane plug 200 out of the capsule 302. The membrane plug 200 may return to its original position after the pressure buildup in the chamber 314 has been vented.

In general, materials suitable for constructing the capsule 302 must be sufficiently rigid to withstand expansion of the osmotic agent 320 without changing its size or shape. Further, the materials should ensure that the capsule 302 will not leak, crack, break, or distort under stress to which it could be subjected during implantation or under stresses due to the pressures generated during operation. The capsule 302 may be formed of chemically inert biocompatible, natural or synthetic materials which are known in the art. The capsule material is preferably a non-bioerodible material which remains in the patient after use, such as titanium. However, the material of the capsule 302 may alternatively be a bioerodible material which bioerodes in the environment after dispensing of the beneficial agent. Generally, preferred materials for the capsule 302 are those acceptable for human implantation.

In general, typical materials of construction suitable for the capsule 302 according to the present invention include non-reactive polymers or biocompatible metals or alloys. The polymers include acrylonitrile polymers such as acrylonitrile-butadiene-styrene terpolymer, and the like; halogenated polymers such as polytetraflouroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the capsule 302 include stainless steel, titanium, platinum, tantalum, gold, and their alloys, as well as gold-plated ferrous alloys, platinum-plated ferrous alloys, cobalt-chromium alloys and titanium nitride coated stainless steel.

A capsule 302 made from the titanium or a titanium alloy having greater than 60%, often greater than 85% titanium, is particularly preferred for the most size-critical applications, for high payload capability and for long duration applications, and for those applications where the formulation is sensitive to body chemistry at the implantation site or where the body is sensitive to the formulation. In certain embodiments, and for applications other than the fluid-imbibing devices specifically described, where unstable beneficial agent formulations are in the capsule 302, particularly protein and/or peptide formulations, the metallic components to which the formulation is exposed must be formed of titanium or its alloys as described above.

The osmotic agent 320 may be in tablet form as shown or may have other shape, texture, density, and consistency. For example, the osmotic agent 320 may be in powder or granular form. The osmotic agent 320 may be, for example, a nonvolatile water soluble osmagent, an osmopolymer which swells on contact with water, or a mixture of the two.

In general, the present invention applies to the administration of beneficial agents, which include any physiologically or pharmacologically active substance. The beneficial agent 322 may be any of the agents which are known to be delivered to the body of a human or an animal such as medicaments, vitamins, nutrients, or the like. Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species. An exemplary list of drugs that may be delivered using the osmotic pump is disclosed in U.S. Pat. No. 6,270,787. The list is incorporated herein by reference.

The beneficial agent 322 can be present in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations may be used. Derivatives such as esters, ethers and amides can also be used. A beneficial agent 322 can be used alone or mixed with other beneficial agents. The beneficial agent 322 may optionally include pharmaceutically acceptable carriers and/or additional ingredients such as antioxidants, stabilizing agents, permeation enhancers, etc.

Figure 2C:
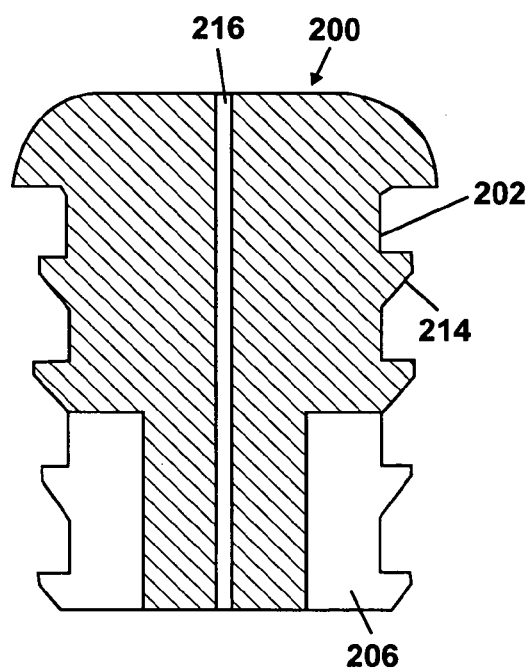
FIG. 2C is a cross-section of a membrane plug according to another embodiment of the invention.

FIG. 2C shows another embodiment of the membrane plug 200. In this embodiment, at least one orifice 216 is formed in the columnar body 202. When the membrane plug 200 is inserted at an end of an osmotic pump, such as osmotic pump (300 in FIG. 3), the orifice 216 allows fluid to pass through the membrane plug 200 to the osmotic agent (320 in FIG. 3) and permeate the osmotic agent (320 in FIG. 3) before the membrane plug 200 is fully hydrated. This has the effect of accelerating the startup phase of the osmotic pump. The size of the orifice 216 is such that fluid can flow through the columnar body 202. The size of the orifice 216 is also such that upon adequate hydration/swelling of the columnar body 202 the orifice 216 becomes occluded, allowing the osmotic function of the system to be fully activated.

The diameter of the orifice 216 depends on the outside diameter of the columnar body 202 of the membrane plug 200, the inside diameter of the capsule (302 in FIG. 3), and the percentage of fluid the membrane plug 200 material will absorb. The diameter of the orifice 216 may be selected based on the assumption that the membrane plug 200 material will expand the same percentage in all directions until it meets a constraint such as the capsule.

The volume, V, of the membrane plug 200 can be expressed as follows:

$$V = \pi L \left(\frac{D}{2}\right)^2 \tag{1}$$

where L is the length of the membrane plug 200 and D is the diameter of the columnar body 202. Multiplying both sides of equation (1) by $(1+b)^3$ gives:

$$V(1+b)^3 = L(1+b)\left(\frac{D(1+b)}{2}\right)^2 \pi \tag{2}$$

where b is the change in the linear dimension of the membrane plug 200 due to fluid absorption. Let c be the change in volume of the membrane plug 200 due to fluid absorption, then:

$$(1+b)^3 = 1+c \tag{3}$$

If the outside diameter of the membrane plug 200 is the same as the inside diameter of the capsule (302 in FIG. 3), then the area of the orifice 216 at time 0 before the plug expands ($A_{o,t=0}$) must be less than the difference between the cross-sectional area of the plug at time 0 before the plug expands ($A_{p,t=0}$) and the cross-sectional area of the plug at time 1 after the plug expands ($A_{p,t=1}$). That is, $$A_{o,t=0} < A_{p,t=1} - A_{p,t=0} \quad (4)$$

where $$A_{o,t=0} = (d/2)^2 \pi \quad (5)$$

where d is the diameter of the orifice before the plug expands (t=0) and $$A_{p,t=0} = (D/2)^2 \pi \quad (6)$$

and $$A_{p,t=1} = [D(1+b)/2]^2 \pi \quad (7)$$

The following expression is obtained by combining equation (3) with equation (7):

$$A_{p,t=1} = (D/2)^2 (1+c)^{2/3} \pi \quad (8)$$

From equations (6) and (8), the difference between the cross-sectional area of the plug at time 0 and time 1 becomes:

$$A_{p,t=1} - A_{p,t=0} = (D/2)^2 [(1+c)^{2/3} - 1] \pi \quad (9)$$

The following expression is obtained by substituting equations (5) and (9) into equation (4) and solving for d:

$$d < \sqrt{(D)^2 [(1+c)^{2/3} - 1]} \quad (10)$$

Thus, for a membrane plug that expands 18% (c=18%) with a columnar diameter of 3 mm (D=3 mm) in a capsule with a diameter of 3 mm, d<1.02 mm. For this example, d is less than 35% of the diameter of the columnar body. Preferably, d is in a range from 0.8 to 33% of the diameter of the columnar body.

The invention typically provides the following advantages. The membrane plug of the invention has a built-in mechanism that prevents its expulsion from an osmotic pump capsule once inserted in the capsule. As a result, additional operations to glue the membrane plug to the capsule or drill holes in the capsule are avoided. Further, any compromise in the operation of the membrane plug due to gluing of the membrane plug to the capsule is avoided. The mechanism for preventing expulsion of the membrane plug from the capsule, i.e., the vent slot(s), can be formed in the membrane plug at the time that the membrane plug is fabricated. For example, if the membrane plug is formed by molding, the mold design would already account for the slot(s) in the membrane plug. Because this solution does not require an additional operation, it should not significantly increase the cost of the osmotic pump. The membrane plug can include an orifice that allows the osmotic agent to start hydrating even before the membrane plug is fully hydrated. This has the effect of accelerating the startup phase of the osmotic pump.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An osmotic pump, comprising:
   a capsule having a first end and a second end and an interior chamber disposed between the first end and the second end, the capsule having at least one delivery port formed at a the first end;
   a membrane plug made of a semipermeable material inserted in an opening at the second end of the capsule remote from the delivery port to provide a fluid-permeable baffler between the interior chamber and an exterior of the capsule;
   wherein the membrane plug has a columnar body bounded externally by a side surface and a base surface and at least one slot formed in the columnar body, the slot being in communication with the base surface and the base surface being in communication with the interior chamber, the slot extending from the base surface and terminating at a non-basal point on the side surface distanced from the base surface to vent pressure from the interior chamber to the exterior of the capsule when the columnar body extends a predetermined distance relative to the second end of the capsule, thereby preventing expulsion of the membrane plug from the second end;
   wherein an orifice traverses an entire length of the membrane plug such that exterior fluid flows into and through the columnar body through the orifice until the orifice becomes occluded due to swelling of the semipermeable material.

2. The osmotic pump of claim 1, wherein the non-basal point is in a range from 10 to 90% of a length of the columnar body.

3. The osmotic pump of claim 1, wherein the non-basal point is in a range from 20 to 80% of a length of the columnar body.

4. The osmotic pump of claim 1, wherein the non-basal point is in a range from 30 to 60% of a length of the columnar body.

5. The osmotic pump of claim 1, wherein the columnar body terminates in an enlarged end cap remote from the base surface, the end cap having a surface for engagement with the second end of the capsule so as to establish a repeatable position of the columnar body in the capsule.

6. The osmotic pump of claim 1, wherein a plurality of protrusions is provided on the surface of the columnar body for engaging an inner surface of the capsule.

7. The osmotic pump of claim 1, wherein the interior chamber is for containing an osmotic agent and the capsule has another interior chamber for containing a beneficial agent.

8. The osmotic pump of claim 7, further comprising a piston movably disposed between the interior chamber for containing the osmotic agent and the interior chamber for containing the beneficial agent.

9. The osmotic pump of claim 1, wherein the delivery port is provided by a diffusion moderator retained in the first end of the capsule.

10. The osmotic pump of claim 1, wherein a diameter of the orifice is less than 35% of a diameter of the columnar body.

11. The osmotic pump of claim 1, wherein a diameter of the orifice is in a range from 0.8 to 33% of a diameter of the columnar body.

12. A membrane plug for use with an osmotic pump having a delivery capsule, comprising:
   a columnar body made of a semipermeable material and adapted for insertion into an opening at an end of the delivery capsule, the columnar body bounded externally by a side surface and a base surface, the side surface adapted for engagement with an inner surface of the capsule, the columnar body being provided with a slot which is in communication with the base surface, the slot extending from the base surface of the columnar body and terminating on a non-basal point on the side surface of the columnar body distanced from the base surface so that pressure can be selectively vented from the base surface to the side surface;

wherein an orifice traverses an entire length of the membrane plug such that exterior fluid flows into and through the columnar body through the orifice until the orifice becomes occluded due to swelling of the semipermeable material.

13. The membrane plug of claim 12, wherein the non-basal point is in a range from 10 to 90% of a length of the columnar body.

14. The membrane plug of claim 12, wherein the non-basal point is in a range from 20 to 80% of the length of the columnar body.

15. The membrane plug of claim 12, wherein the non-basal point is in a range from 30 to 60% of a length of the columnar body.

16. The membrane plug of claim 12, further comprising an enlarged end cap formed on the columnar body, the end cap having a surface for engagement with an end of the capsule so as to achieve a repeatable position of the columnar body in the capsule.

17. The membrane plug of claim 12, wherein a plurality of protrusions is provided on the surface of the columnar body for engagement with the inner surface of the capsule.

18. The membrane plug of claim 12, wherein a diameter of the orifice is less than 35% of a diameter of the columnar body.

19. The membrane plug of claim 12, wherein a diameter of the orifice is in a range from 0.8 to 33% of a diameter of the columnar body.

* * * * *